US009996676B2

(12) United States Patent
Vik et al.

(10) Patent No.: US 9,996,676 B2
(45) Date of Patent: *Jun. 12, 2018

(54) ASSOCIATING AN INFORMATION READER AND A MEDICAL DEVICE

(71) Applicant: CareFusion 303, Inc., San Diego, CA (US)

(72) Inventors: Daniel Vik, Sunnyvale, CA (US); Sreelal Chandrasenan, San Diego, CA (US); Gregory Borges, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/404,503

(22) Filed: Jan. 12, 2017

(65) Prior Publication Data

US 2017/0193188 A1  Jul. 6, 2017

Related U.S. Application Data

(63) Continuation of application No. 14/733,885, filed on Jun. 8, 2015, now Pat. No. 9,547,751, which is a continuation of application No. 13/275,005, filed on Oct. 17, 2011, now Pat. No. 9,053,520.

(51) Int. Cl.
*G06K 7/10* (2006.01)
*G06F 19/00* (2018.01)
*G06K 7/14* (2006.01)

(52) U.S. Cl.
CPC ..... *G06F 19/3456* (2013.01); *G06K 7/10366* (2013.01); *G06K 7/1413* (2013.01)

(58) Field of Classification Search
CPC ............ G06F 19/327; G06F 17/30879; G06F 19/3406; G06Q 50/22
USPC .............. 235/435, 451, 454, 462.01, 462.15, 235/462.41, 462.45, 462.46, 470, 472.01, 235/472.02
See application file for complete search history.

(56) References Cited

U.S. PATENT DOCUMENTS

| 4,476,381 A * | 10/1984 | Rubin ................... B01L 3/5453 235/375 |
| 7,813,822 B1 * | 10/2010 | Hoffberg ............ G06K 9/00369 381/73.1 |
| 7,839,266 B2 * | 11/2010 | Hoglund ............... G06F 19/327 340/10.1 |

(Continued)

FOREIGN PATENT DOCUMENTS

| JP | 2007-310759 A | 11/2007 |
| JP | 2011-065481 A | 3/2011 |

(Continued)

*Primary Examiner* — Paultep Savusdiphol
(74) *Attorney, Agent, or Firm* — Mintz Levin Cohn Ferris Glovsky and Popeo, P.C.; Fred C. Hernandez

(57) ABSTRACT

A device agent including an information accessor for accessing association information obtained via an information reader. The association information includes medical device information for uniquely identifying the medical device, and device agent information for facilitating in an association between the medical device and the information reader. The device agent also includes an associator for associating the medical device and the information reader based on the association information.

20 Claims, 5 Drawing Sheets

(56) References Cited

U.S. PATENT DOCUMENTS

| | | | |
|---|---|---|---|
| 8,058,986 B2* | 11/2011 | Klabunde | A61B 5/0205 340/10.1 |
| 2003/0135388 A1* | 7/2003 | Martucci | A61M 5/142 705/2 |
| 2003/0140928 A1 | 7/2003 | Bui et al. | |
| 2003/0173405 A1 | 9/2003 | Wilz et al. | |
| 2004/0104271 A1* | 6/2004 | Martucci | A61M 5/142 235/472.01 |
| 2004/0193453 A1* | 9/2004 | Butterfield | A61M 5/172 705/2 |
| 2004/0243434 A1* | 12/2004 | Peterka | G06F 19/327 705/2 |
| 2005/0108057 A1 | 5/2005 | Cohen et al. | |
| 2005/0149350 A1* | 7/2005 | Kerr | G06F 19/327 705/2 |
| 2005/0182661 A1* | 8/2005 | Allard | G06F 19/322 705/3 |
| 2007/0267475 A1* | 11/2007 | Hoglund | G06F 19/327 235/375 |
| 2007/0300063 A1* | 12/2007 | Adams | G06F 21/35 713/168 |
| 2008/0149701 A1 | 6/2008 | Lane | |
| 2008/0221930 A1* | 9/2008 | Wekell | A61B 5/02055 705/3 |
| 2008/0303638 A1* | 12/2008 | Nguyen | G06F 19/3462 340/10.42 |
| 2009/0231124 A1* | 9/2009 | Klabunde | A61B 5/0205 340/539.12 |
| 2010/0169120 A1 | 7/2010 | Herbst et al. | |

FOREIGN PATENT DOCUMENTS

| | | |
|---|---|---|
| KR | 10-2004-0073560 | 8/2004 |
| WO | WO-00/16211 A1 | 3/2000 |
| WO | WO-03/060805 A2 | 7/2003 |

* cited by examiner

ASSOCIATING AN INFORMATION READER AND A MEDICAL DEVICE

CROSS REFERENCE TO RELATED APPLICATIONS

This application is a continuation of U.S. patent application Ser. No. 14/733,885, filed on Jun. 8, 2015 entitled "Associating An Information Reader And A Medical Device", issuing on Jan. 17, 2017 as U.S. Pat. No. 9,547,751, which is a continuation of U.S. patent application Ser. No. 13/275,005 (now issued as U.S. Pat. No. 9,053,520), filed Oct. 17, 2011, entitled "Associating An Information Reader And A Medical Device", the contents of which are herein incorporated by reference in their entirety.

BACKGROUND

Barcode systems are often used in medical environments to ensure safety. For example, a barcode system can ensure that correct drugs are given to the proper patient or only authorized personnel can administer the proper medical protocol to a patient.

Oftentimes, a barcode scanner is permanently associated with a single medical device. For example, the barcode scanner is physically attached to the medical device. As a result, the flexibility of a medical environment is limited because it is difficult to share barcode scanners with other medical devices.

Also, a floating barcode is utilized in BCMA systems. For floating barcode devices, barcode scans are sent to a centralized system. The scanning is only done to get information (e.g., device id, similar to when you scan a badge), and the information is used in backend systems to perform some general work. However, the intent and workflow, regarding the floating barcode in a BCMA system, is not for directing subsequent barcode scans to a particular device.

Moreover, a barcode scanner may be unable to directly communicate with a medical device because of limited communication capabilities.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

In general, information readers are associated with medical devices to ensure safety in a medical environment. The discussion below will describe a variety of means to associate an information reader with medical device(s). In particular, the discussion will first describe the components in a medical environment. Then the discussion will describe functionality of the components during use of the medical environment.

It is understood that "association," as used herein, for example, the association between an information reader and a medical device, generally describes the communicative coupling between the devices. As a result of the association, information, obtained by the information reader, is able to be routed to the associated device(s).

Figure 1:
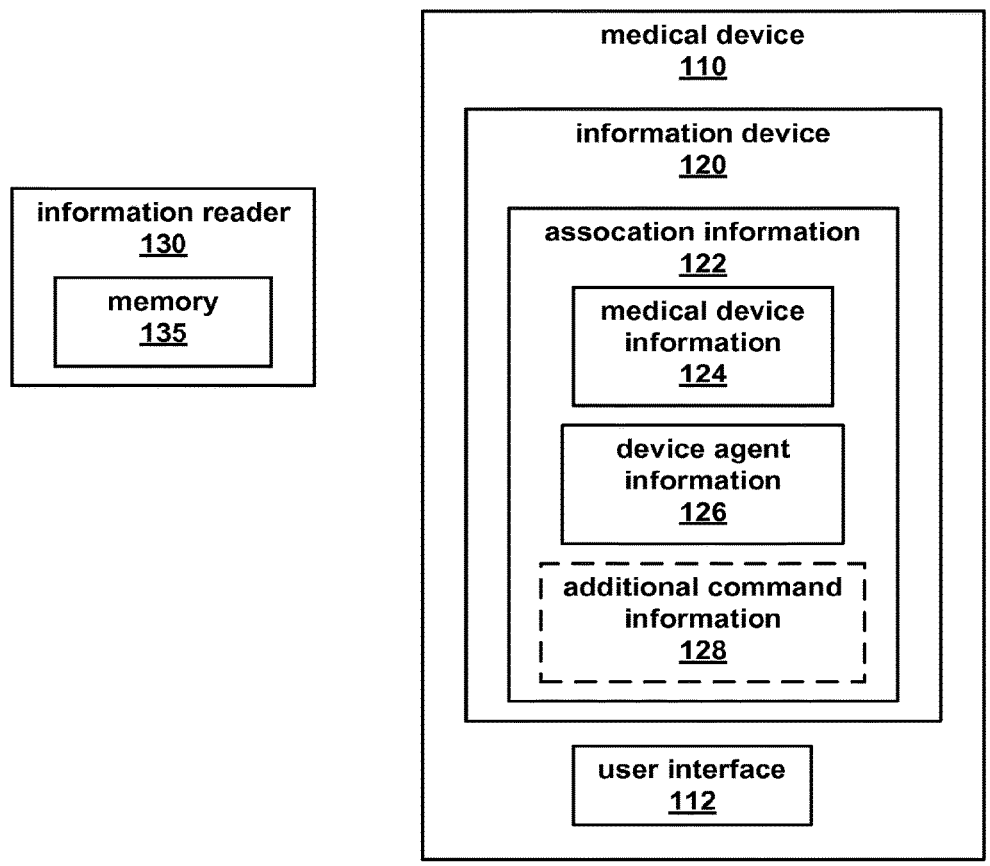
FIGS. 1-3 illustrate embodiments of a medical system.

FIG. 1 depicts an embodiment of medical environment 100. Medical environment 100 includes medical device 110, information reader 130 and device agent 140.

Information reader 130 is any device that is capable of reading information and also able to be associated with a medical device. For example, information reader 130 can be, but is not limited to, a barcode scanner, a radio-frequency identification (RFID) reader. Moreover, information reader 130 can be any device (e.g., a mobile device) with barcode scanning and/or RFID reading capabilities.

Medical device 110 can be any medical device(s) that is able to be associated with an information reader. For example, medical device is a ventilator, infusion pump, etc.

In general, association information 122 is utilized to facilitate in the association between information reader 130 and medical device 110. Association information 122 includes medical device information 124, device agent information 126 and optionally, additional command information 128.

Also, in various embodiments, association information 122 includes a cookie (data element) that appends to any consecutive scan after an association generated. The cookie allows the destination device (and/or routing devices) to uniquely identify scans intended for the destination device.

Medical device information 124 includes any information or signature that uniquely identifies medical device 110 and/or any other medical devices. For example, medical device information 124 can be, but is not limited to, model number, serial number, Media Access Control address (MAC) address, Internet Protocol (IP) address, etc.

Device agent information 126 includes any information that can be utilized by device agent 140 (or any other device agent) to properly route information, obtained by information reader 130, to medical device 110. For example, device agent information 126 can include, but is not limited to, agent name, connectivity parameters (e.g., IP/Bluetooth parameters), commands for routing information to a specific device (e.g., medical device 110), and authentication information.

Additional command information 128 can be any additional information (other than medical device information 124 and device agent information 126) that provides commands for routing information obtained by information reader 130. For example, additional command information 128 can provide commands to device agent 140 to route information to other devices. In another example, command information 128 can include disassociation information (e.g., disassociate immediately, or after X seconds).

Association information 122 is able to be read or obtained by information reader 130 via information device 120. In various embodiments, information device 120 is a barcode (static or dynamic) or an RFID tag. Accordingly, association information 122 is presented as a static barcode, a dynamic barcode or an RFID tag. As such, information reader 130 (e.g., a barcode reader or an RFID reader) is able to read or obtain association information 122 via information device 120.

In one embodiment, information device 120 is attached to medical device 110. For instance, a barcode or an RFID tag is physically attached (e.g., adhered) to an infusion pump.

In another embodiment, information device 120 is a display for rendering a scannable barcode. In such an embodiment, association information 122 is dynamically displayed on information device 120. Also, the display can be integrated within medical device 110 or can be separate, but proximate to, medical device 110. It should be understood that the rendered barcode (displayed on the display) contains the association information 122 describe above.

Device agent 140 is an agent or proxy for medical device 110 and is utilized to facilitate in the association between information reader 130 and medical device 110. Device agent 140 includes information accessor 142, router 144, associator 146, dissassociator 148, and optionally, proximity estimator 149.

Information accessor 142 is for accessing association information 122 via information reader 130.

Associator 146 is configured for associating medical device 110 and information reader 130 based on association information 122. Disassociator 148 is for disassociating an established association between information reader 130 and medical device 110.

Proximity estimator 146 is for estimating a proximity or distance between medical device 110 and information reader 130.

Router 144 is for routing subsequent information (e.g., information from a scanned barcode on a bottle of medicine) to medical device 110.

During use of medical environment 100, information reader 130 and medical device 110 are initially unassociated. As such, any information obtained by information reader 130 would not necessarily be routed to medical device 110.

In order to associate information reader 130 and medical device 110, information reader 130 reads association information 122. In particular, medical device information 124 and device agent information 126. For example, a handheld barcode scanner scans a barcode that includes the serial number of medical device 110 and the MAC address for device agent 140.

Information reader 130 communicates with device agent 140 in a variety of ways. In various examples, information reader 130 communicates with device agent 140 by Universal Serial Bus (USB), internet, Wi-Fi, Bluetooth, etc.

Information accessor 142 accesses association information 122. Associator 150 obtains association information 122 and associates information reader 130 and medical device 110 based on association information 122. For example, associator 150 generates an association based on the received serial number of medical device 110 and the MAC address for device agent 140.

In one embodiment, associator 146 automatically generates an association in response to the obtained association information 122. In another embodiment, associator 146 automatically generates an association in response to user input, which will be described in detail below.

As a result of the generated association, router 144 routes subsequent information obtained by information reader 130 to medical device 110. For example, batches of medication are intended to be infused into Patient A. Barcodes on the batches of medication are scanned by information reader 130. The information from the scanned barcodes are then routed to medical device 110 (e.g., an infusion pump) to facilitate in the infusion of the drugs into Patient A.

In one embodiment, information reader 130 obtains information prior to an established association with medical device 110. For example, information reader 130 obtains information by scanning barcodes on batches of medicine for Patient A. The information is stored in memory 135. Memory 135 can be located within information reader 130 or other locations, such as a server, within medical environment 100.

In response to an association between information reader 130 and medical device 110 (established by associator 146), the information (obtained prior to association) stored in memory 135 is routed to medical device 110.

In various embodiments, the association is a logical peer-to-peer association between information reader 130 and medical device 110. FIG. 1 depicts an association through device agent 140. However, in various other embodiments, the association can utilize point-to-point radio technology on a network (e.g., a local area network (LAN), a wireless LAN (WLAN), or a personal area network (PAN) (e.g., Bluetooth or Zigbee)). In an embodiment of a PAN, direct communication between information reader 130 and medical device 110 is established without requiring any network infrastructure.

Figure 4:
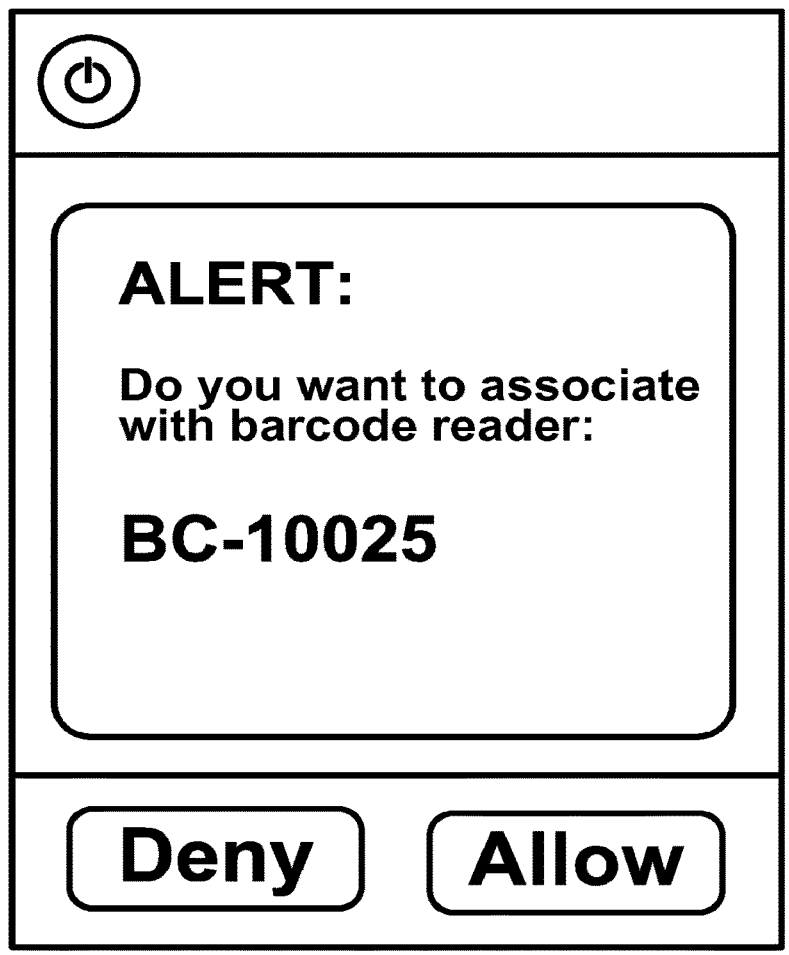
FIG. 4 illustrates an embodiment of displayed information.

Referring now to FIG. 4, to enhance safety and control (enabled or disabled through device configuration) an acknowledgment dialog 400 is displayed on user interface 112 of medical device 110.

A user is prompted to accept the attempted association. If the user chooses to deny the association attempt, medical device 110 will not accept subsequent information (e.g., subsequent barcode scans) from information reader 130, unless a new authentication is performed and accepted.

Referring again to FIG. 1, disassociator 148 terminates or disassociates the association between information reader 130 and medical device 110. In order to reduce the likelihood of undesired information to be routed to a medical device, provisions are added to limit the duration that the association is effective.

For example, a disassociation of an information reader from a medical device can be accomplished via a user interface of the information reader and/or medical device.

Disassociation can automatically occur after a pre-determined amount of time from association. For example, a disassociation automatically occurs after four hour from the time of association.

Disassociation can occur after a pre-determined amount of time from the last scan. For example, a disassociation automatically occurs after one hour from the last scan of the information reader.

Disassociation can occur in response to the devices exceeding a pre-determined maximum distance. For example, proximity estimator 149 estimates the proximity between information reader 130 and medical device 110. In response to medical device 110 and information reader 130 exceeding a pre-determined maximum distance (e.g., 40 feet), medical device 110 and information reader 130 are disassociated.

Disassociation can automatically occur in response if a connection (e.g., wireless) between the devices is lost.

Disassociation can automatically occur in response to completed work flow. For example, disassociation occurs after successful drug scanning, and patient ID and/or clinician ID are associated with the medical device.

Disassociation can occur if information reader reads/obtains association information of another medical device.

Figure 2:
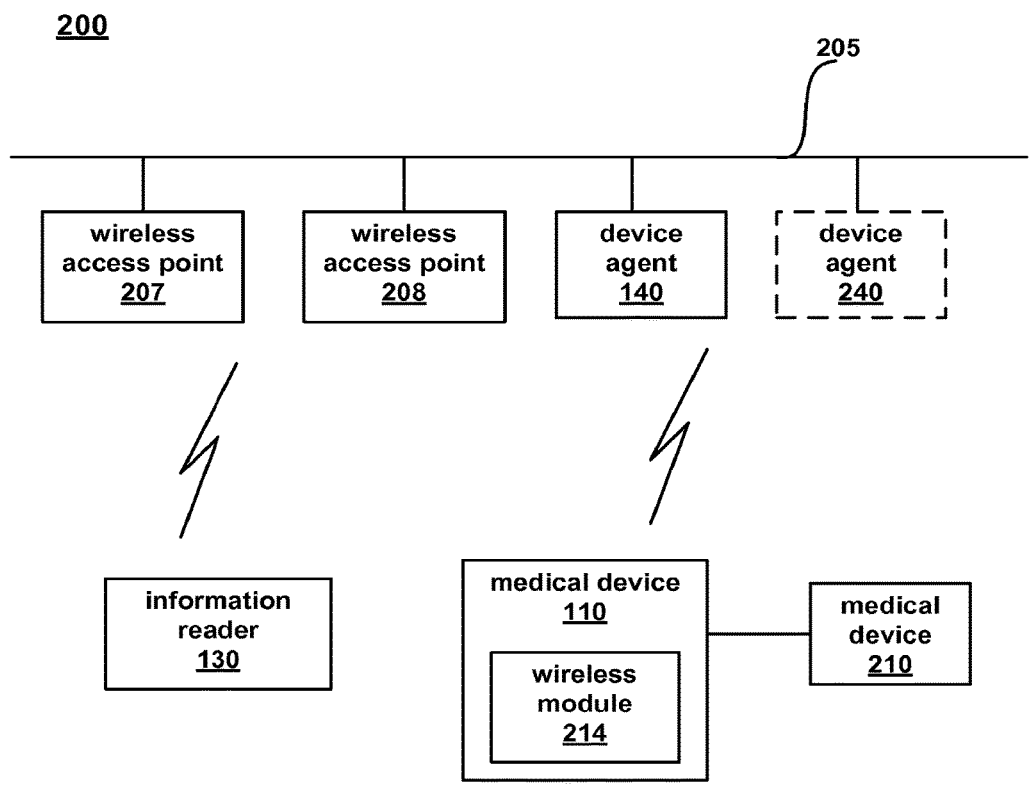

Referring to FIG. 2, medical environment 200 includes network 205, wireless access points 207 and 208, device agents 140 and 240, information reader 130, and medical devices 110 and 210.

Medical device 110 also includes wireless module 214. Wireless module 214 allows for medical device 110 to wirelessly connect to network 205 via wireless access points 207 and/or 208.

Also, medical device 110 is connected to or associated with other medical devices, such as medical device 210. For example, medical device 110 is a first Large Volume Parenterals (LVP) device and medical device 210 is a second LVP device.

Moreover, medical device 210 does not have the capability to directly communicate with information reader 130. Although two medical devices are depicted in FIG. 2, it should be appreciated that any number of medical devices can be connected to or associated with one another.

During use of medical environment 200, information reader 130 can be associated with medical device 110 in the same manner as described above.

In one embodiment, information 130 can also be associated with medical device 210. In order to associate information reader 130 and medical device 210, information reader 130 reads association information 122 which is presented by medical device 110. In particular, information reader 130 reads medical device information 124 which uniquely identifies medical device 210.

Information accessor 142 accesses association information 122. Associator 150 obtains association information 122 and subsequently associates information reader 130 and medical device 210 based on association information 122. As a result of the generated association, router 144 routes subsequent information obtained by information reader 130 to medical device 210.

It should be appreciated that information reader 130 can be concurrently associated with medical devices 110 and 210.

It may be desired that medical devices 110 and 210 are to utilize device agent 240 rather than device agent 140. For example, medical devices 110 and 210 initially utilize device agent 140. However, for purposes of testing the medical devices, device agent 240 (e.g., a testing device agent) is utilized.

Accordingly, information reader 130 reads association information 122. In particular, information reader 130 reads device agent information 126 which identifies device agent 240. As a result, subsequent information obtained by information reader 130 is routed to medical device 110 and/or 210 via router 240 (rather than device agent 140).

A device agent (e.g., device agent 140) can optionally add functionality to the system. The device agent can be a physical device or virtual device agent, which has close communication with the medical devices. The device agent can manage the scan workflows and rules such as valid scan, valid sequence of scans, association and disassociation of barcode. A valid scan can include valid data in the scan, a scan supported by a medical device such as intermittent infusion or PCA infusion not supported by the device. A valid sequence may include scanning patient ID, clinical ID and a drug scan.

A device agent can determine when to associate the barcode and when to disassociate the barcode. A device agent may perform preprocessing of the scan before sending to medical device such as mapping the drug entry ID to drug name or order ID to order details. In this case, the device agent will store drug library and order information.

Figure 3:
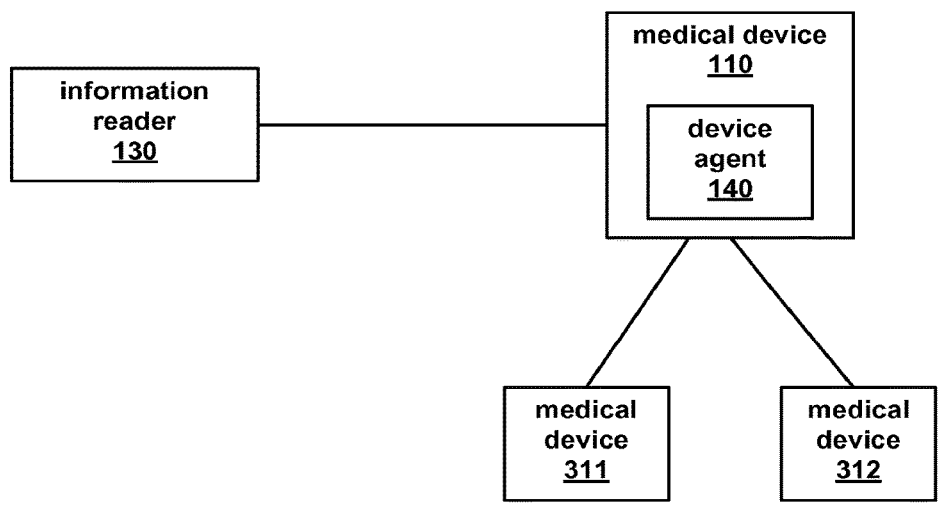

Referring to FIG. 3, an embodiment of medical environment 300 is depicted. Medical environment 300 includes information reader 130 and medical devices 110, 310 and 312.

In such an embodiment, medical device 110 includes device agent 140. In other words, medical device 110 also functions as device agent 140. For example, medical device 110, 310 and 312 are devices in a medical device rack system. As such, medical device 110 acts as a proxy or device agent for medical devices 311 and 312 because medical devices 311 and 312 do not have the capability to directly communicate with information reader 130.

During use of medical environment 300, information reader 130 can be associated with medical device 310 in the same manner as described above.

In another embodiment, information 130 can also be associated with medical devices 311 and 312. In order to associate information reader 130 and medical devices 311 and/or 312, information reader 130 reads association information 122 which is presented by medical device 310. In particular, information reader 130 reads medical device information 124 which uniquely identifies medical devices 311 and/or 312.

Information accessor 142 accesses association information 122. Associator 150 obtains association information 122 and subsequently associates information reader 130 and medical devices 311 and/or 312 based on association information 122. As a result of the generated association, router 144 routes subsequent information obtained by information reader 130 to medical devices 311 and/or 312.

Figure 5:
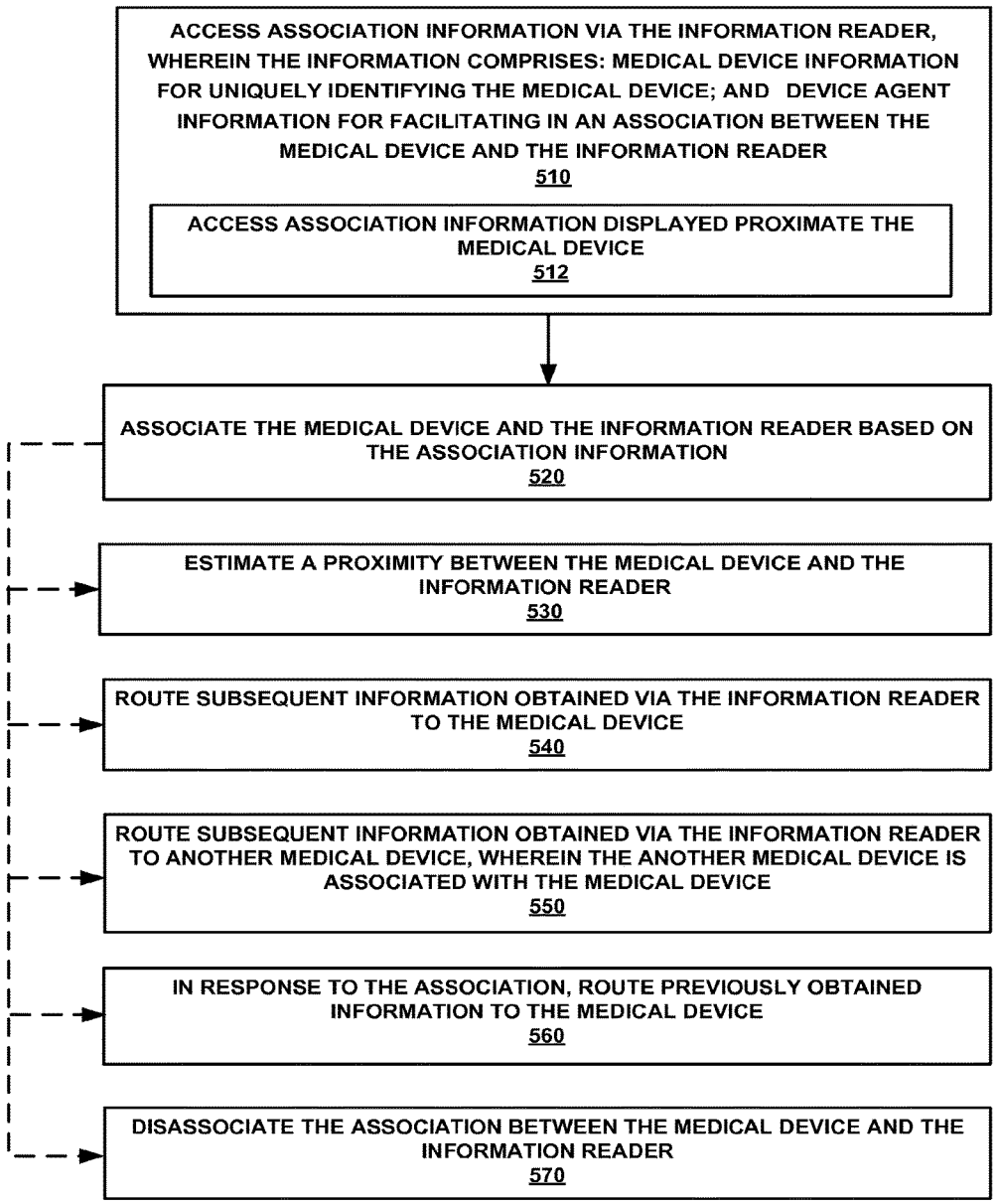
FIG. 5 illustrates an embodiment a method for associating an information reader and medical device.

FIG. 5 depicts an embodiment of a method 500 for associating an information reader and a medical device. In various embodiments, method 500 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 500 is performed at least by device agent 140 and/or medical device 110, as depicted in FIG. 1.

At 510 of method 500, association information is accessed via the information reader, wherein the information comprises medical device information for uniquely identifying the medical device, and device agent information for facilitating in an association between the medical device and the information reader.

For example, association information 122 is scanned by information reader 130 (e.g., barcode scanner). In particular, association information 122 includes medical device information 124 which is a unique signature of medical device 110 and device agent information 126 which can include agent name, connectivity parameters (e.g., IP/Bluetooth parameters), and/or commands for routing information to a specific device.

In one embodiment, at 512, association information displayed proximate the medical device is accessed. For example, association information 122 is presented by information device 120 (e.g., dynamic barcode) which is physically attached to medical device 110.

At 520, the medical device and the information reader are associated based on the association information. For example, associator 146 associates information reader 130 and medical device 110 based on association information 122.

At 530, a proximity is estimated between the medical device and the information reader. For example, information reader 130 and medical device 110 are disassociated in response to the devices exceeding a maximum distance. It should be understood that the proximity estimation utilized for disassociation is just one embodiment for managing disassociation. In particular, the proximity estimation is not required in all embodiments.

At 540, subsequent information obtained via the information reader is routed to the medical device. For example, router 144 routes information obtained by scanning barcodes on batches of medicine to medical device 110.

At 550, subsequent information obtained via the information reader is routed to another medical device, wherein the another medical device is associated with the medical device. For example, router 144 routes information obtained by scanning barcodes on batches of medicine to medical devices 311 and/or 312.

At 560, in response to the association, route previously obtained information to the medical device. For example, prior to association, information reader 130 obtains information and the information is stored in memory 135. In response associator 146 establishing an association between information reader 130 and medical device 110, the information stored in memory 135 is routed to medical device 110.

At 570, a disassociation occurs between the medical device and the information reader. For example, disassociation occurs in response to a lost wireless connection between medical device 110 and information reader 130.

Various embodiments of the present invention are thus described. While the present invention has been described in particular embodiments, it should be appreciated that the present invention should not be construed as limited by such embodiments, but rather construed according to the following claims.

The invention claimed is:

1. A medical device apparatus comprising:
at least one data processor; and
memory storing instructions which, when executed by the least one data processor, result in operations comprising:
obtaining association information via an information reader, wherein the association information comprises:
medical device information related to identification of a medical device, and
routing information related to facilitation of an association between the medical device and the information reader; and
associating the medical device and the information reader based on the association information,
wherein at least the apparatus and the information reader are different devices.

2. The medical device apparatus of claim 1, wherein the association information further comprises a data element that is appended to one or more scans after the association of the medical device and the information reader that allow for the one or more scans to be identified as being intended for the medical device.

3. The medical device apparatus of claim 2, the operations further comprising:
routing subsequent information obtained via the information reader to the medical device using the data element in the one or more scans.

4. The medical device apparatus of claim 1, the operations further comprising:
routing previously obtained information to the medical device, in response to the association between the medical device and the information reader.

5. The medical device apparatus of claim 1, wherein the information reader is at least one of: a barcode scanner, an optical scanner, and a radio-frequency identification (RFID) reader.

6. The medical device apparatus of claim 1, the operations further comprising:
disassociating the association between the medical device and the information reader.

7. The medical device apparatus of claim 6, the operations further comprising:
determining a distance between the medical device and the information reader,
wherein the medical device and the information reader are disassociated when the determined distance between the medical device and the information reader exceeds a pre-determined maximum distance.

8. A method comprising:
accessing, by a device agent, association information obtained via an information reader, wherein the association information comprises:
medical device information related to identification of a medical device, and
routing information related to facilitation of an association between the medical device and the information reader; and
associating, by the device agent, the medical device and the information reader based on the association information,
wherein at least the device agent and the information reader are different devices.

9. The method of claim 8, wherein the association information further comprises a data element that is appended to one or more scans after the association of the medical device and the information reader that allow for the one or more scans to be identified as being intended for the medical device.

10. The method of claim 9 further comprising:
routing subsequent information obtained via the information reader to the medical device using the data element in the one or more scans.

11. The method of claim 8 further comprising:
routing previously obtained information to the medical device, in response to the association between the medical device and the information reader.

12. The method of claim 8, wherein the information reader is at least one of: a barcode scanner, an optical scanner, and a radio-frequency identification (RFID) reader.

13. The method of claim 8 further comprising:
disassociating the association between the medical device and the information reader.

14. The method of claim 13 further comprising:
determining a distance between the medical device and the information reader,
wherein the medical device and the information reader are disassociated when the determined distance between the medical device and the information reader exceeds a pre-determined maximum distance.

15. A non-transitory computer-readable medium containing instructions to configure a processor to perform operations comprising:
    accessing, by a device agent, association information obtained via an information reader, wherein the association information comprises:
        medical device information related to identification of a medical device, and
        routing information related to facilitation of an association between the medical device and the information reader; and
    associating, by the device agent, the medical device and the information reader based on the association information,
    wherein at least the device agent and the information reader are different devices.

16. The non-transitory computer-readable medium of claim 15, wherein the association information further comprises a data element that is appended to one or more scans after the association of the medical device and the information reader that allow for the one or more scans to be identified as being intended for the medical device, and
    wherein the operations further comprise:
        routing subsequent information obtained via the information reader to the medical device using the data element in the one or more scans.

17. The non-transitory computer-readable medium of claim 15, the operations further comprising:
    routing previously obtained information to the medical device, in response to the association between the medical device and the information reader.

18. The non-transitory computer-readable medium of claim 15, wherein the information reader is at least one of: a barcode scanner, an optical scanner, and a radio-frequency identification (RFID) reader.

19. The non-transitory computer-readable medium of claim 15, the operations further comprising:
    disassociating the association between the medical device and the information reader.

20. The non-transitory computer-readable medium of claim 19, the operations further comprising:
    determining a distance between the medical device and the information reader,
    wherein the medical device and the information reader are disassociated when the determined distance between the medical device and the information reader exceeds a pre-determined maximum distance.

\* \* \* \* \*